United States Patent
Wang

(10) Patent No.: US 7,655,611 B2
(45) Date of Patent: Feb. 2, 2010

(54) STRUCTURAL FAMILY ON NON-IONIC CARBOHYDRATE BASED SURFACTANTS (NICBS) AND A NOVEL PROCESS FOR THEIR SYNTHESIS

(75) Inventor: Zerong Wang, Houston, TX (US)

(73) Assignee: The University of Houston System, Houston, TX (US)

(*) Notice: Subject to any disclaimer, the term of this patent is extended or adjusted under 35 U.S.C. 154(b) by 0 days.

(21) Appl. No.: 11/303,056

(22) Filed: Dec. 14, 2005

(65) Prior Publication Data

US 2006/0154846 A1    Jul. 13, 2006

Related U.S. Application Data

(60) Provisional application No. 60/635,739, filed on Dec. 14, 2004.

(51) Int. Cl.
*C11D 3/22* (2006.01)
*C11D 3/26* (2006.01)
*A61K 8/73* (2006.01)

(52) U.S. Cl. ............... 510/470; 510/474; 510/499; 510/535; 424/488; 424/70.13

(58) Field of Classification Search ............ 510/470, 510/474, 499, 535; 424/488, 70.13
See application file for complete search history.

(56) References Cited

U.S. PATENT DOCUMENTS

| | | |
|---|---|---|
| 675,330 A | 5/1901 | Ihlenfeldt |
| 5,500,153 A | 3/1996 | Figueroa et al. |
| 5,531,915 A | 7/1996 | Perkins |
| 5,622,925 A | 4/1997 | De Buzzaccarini et al. |
| 5,723,426 A | 3/1998 | Zhen et al. |
| 5,780,607 A * | 7/1998 | Goodnow et al. .......... 536/22.1 |
| 5,827,813 A | 10/1998 | Hartman et al. |
| 5,858,948 A | 1/1999 | Ghosh et al. |
| 5,935,271 A | 8/1999 | Lappas et al. |
| 5,942,485 A | 8/1999 | Kemen |
| 6,087,321 A | 7/2000 | Panandiker et al. |
| 6,184,188 B1 | 2/2001 | Severns et al. |
| 6,214,786 B1 | 4/2001 | Randall et al. |
| 6,251,845 B1 | 6/2001 | Herbots et al. |
| 6,281,181 B1 | 8/2001 | Vinson et al. |
| 6,303,563 B1 | 10/2001 | De Buzzaccarini et al. |
| 6,369,024 B1 | 4/2002 | Panandiker et al. |
| 6,376,445 B1 | 4/2002 | Bettiol et al. |
| 6,384,011 B1 | 5/2002 | Leupin et al. |
| 6,407,053 B1 | 6/2002 | Randall et al. |
| 6,589,926 B1 | 7/2003 | Vinson et al. |
| 6,669,828 B2 | 12/2003 | Fritz-Langhals |
| 6,686,329 B1 | 2/2004 | Salager |
| 6,733,538 B1 | 5/2004 | Panandiker et al. |
| 6,774,099 B1 | 8/2004 | Scheibel et al. |

* cited by examiner

*Primary Examiner*—Brian P Mruk
(74) *Attorney, Agent, or Firm*—Robert W. Strozier

(57) ABSTRACT

A novel composition of matter as well as a straightforward single step process for the preparation or production of said novel composition of matter is disclosed. The composition affords a new type of nonionic carbohydrate based surfactants (NICBS), a type of biodegradable neutral surfactant. The produced surfactant compositions have both neutral, but polar polyhydroxyl heads and nonpolar tails that are linked via at least one amide bond and possibly another ester bond as well.

23 Claims, No Drawings

STRUCTURAL FAMILY ON NON-IONIC CARBOHYDRATE BASED SURFACTANTS (NICBS) AND A NOVEL PROCESS FOR THEIR SYNTHESIS

RELATED APPLICATIONS

The present application claims provisional priority of U.S. Provisional Application Ser. No. 60/635,739, filed 14 Dec. 2004.

BACKGROUND OF THE INVENTION

1. Field of the Invention

The present invention relates to a new composition and a novel process to prepare or produce such compositions as well as analogous ones.

More particularly, the present invention relates to a new composition and a novel process to prepare or produce such compositions, where the composition includes a hydrophilic part and a hydrophobic part that is suitable for use as a detergent, a surfactant or an emusilfier component, and for the construction of cellular membranes or any membrane or organic film. The compositions are neutral, where the hydrophilic part and hydrophobic part are connected through at least an amide bond or an ester bond. The process to produce the compositions is a novel chemical reaction between a carbohydrate, or acyl group or ether group protected carbohydrate and any of nitriles containing long or short hydrocarbon chains; with or without branching; either saturated or unsaturated; with or without cyclic or aromatic ring. This process uses an acid to promote the conversion rate with or without a salt from group IB metal. The process to produce such composition of matter can undergo in an inert solvent or without any solvent in presence. The process uses a high speed mixing equipment.

2. Description of the Related Art

Surfactants or so-called surface active agents, are types of molecules that can reduce the surface tension of water or other molecules, and can used as detergents, emulsifiers, etc. By chemical definition molecules that are surfactants are molecules that structurally possess a hydrophilic (or lipophobic) component and a hydrophobic (or lipophilic) component. [1] In general the properties of surfactants fall into two broad categories: adsorption and aggregation (or self-assembly). [2] The adsorption properties of surfactants are those that allow the surfactant molecules to be found at the interface between immiscible or only slightly miscible phases such as an oil phase and a water phase, or a water phase and an air phase. It is this latter molecular property that leads to the macroscopic properties possessed by the surfactant such as wetting, foaming, detergency and emulsification. [3] In contrast, aggregation or self-assembly is the tendency for surfactant molecules to organize themselves into extended structures in water. This includes the formation, for example, of micelles, bilayers, liposome and liquid crystals etc. [4] These structures are formed when the hydrophobic parts of surfactants cluster together. When the hydrophilic component is larger than the lipophilic component, micelles are likely to form; by comparison, if the size of hydrophilic component is comparable to the size of the lipophilic component, then bilayers, liposome and membrane structures will form. [5]

The hydrophobic component of commonly used surfactants is long hydrocarbon chains containing between 4 to 20 carbons. An increase in the number of carbons beyond 20 usually has associated with its higher toxicity. [6] By contrast, the hydrophilic component of a surfactant can be either polar or carry a charge (positive or negative or amphoteric). Consequently, surfactants are usually classified into one of four general categories: cationic surfactants, anionic surfactants, neutral or nonionic surfactants, and amphoteric surfactants. The cationic surfactants have a positive charge on the head group when dissolved in water, for example, the carrying of a positively charged ammonium pendent; anionic surfactants will have negatively charged groups as head groups when dissolving in water, (e.g., a sulfate, phosphate, or carboxylate group etc.); nonionic surfactants can have either polyethylene glycols or carbohydrates as polar head groups, and amphoteric surfactants can have positive charges and weak bascity or vice versa. Surfactants, when used as detergents, can form micelles and engulf grease, or oily stains from commonly used clothing materials, so that they can be washed away from the clothes. Similarly, when surfactants are used as emusilfiers, they accumulate on the oil/water interface and prevent coalescing of oil droplets. These emulsifiers can create and maintain the thereby formed emulsions for hours (e.g., salad dressing), months, or years (e.g., medicinal or cosmetic cream). [7]

It is known that long-term exposure to anionic surfactants has been linked to swelling of the skin and skin irritation. Therefore, it is common to add alkyldimethylamine oxide, which is known to depress skin irritation factors, to anionic surfactants. [8] Because, or in spite of this need during manufacture of anionic surfactants, anionic surfactants are generally avoided in cosmetic products. Cationic surfactants are typically used in things like hair-conditioner and fabric softeners. [9] The fatty amine salts proved quite useful in blends with nonionic surfactants, giving good stability over a range of pH levels. Cationic surfactants are generally rated as being more irritating to the skin than anionic surfactants, probably because of their strong ability to adsorb to negatively charged materials on skin, such as proteins and nucleic acid [10] and the cationic surfactants are also not biodegradable. [9] In contrast, the nonionic surfactants are more user friendly, and have much fewer problems with respect to allergic reactions or skin irritation. Thus, the latter type of surfactants are ubiquitous in foods and drinks as well as pharmaceuticals and skin-care products. [11] It is believed that these surfactants have mild negative effects on the skin even at high loading concentrations and long-term exposure. It is because of such features, that the nonionic surfactants are getting more and more use in current processes that demand surfactants. This is especially true for those type of nonionic surfactants that originate from carbohydrates.

Carbohydrate-containing surfactants fall into three distinctly different classes: esters, acetals and amides, and examples of these such as the alkyl glucamides, were not commercialized until the 1990s. [12] Currently, alkyl sugaramides are manufactured in two steps: reductive amination of a carbohydrate with an alkylamine, followed by the acylation of the resulting N-glycosides; [13] similarly, gluconamides, the "reverse glucamides" are also produced in two steps: the oxidation of a carbohydrate leading to lactone or aldonic acid followed by reaction with alkyl amines to form gluconamides. [14] In both processes opening of the carbohydrate ring occurs. However, a carbohydrate-containing nonionic surfactant with an amide linkages to the ring of carbohydrate through a N-glycosidic bond, without opening of the carbohydrate ring is neither known, or suggested in the literature.

Since the aforementioned type of nonionic surfactants have the amide bond linking the hydrophilic and lipophilic components via a N-glycosidic bond, it would be much easier to biodegrade than, for example, alkylpolyglucosides and probably also much more susceptible to biodegradation that either the alkyl glucamides or aldonamides as well. The amide bond in this new structural type of surfactant can be also digested by enzymes currently used in detergent formulation, in a manner similar to the degradation of other proteins by those enzymes. In addition, the biodegradation components from this type of novel surfactants are essentially carbohydrates and fatty acids, both of which are tolerable to humans, animals and the environment. This new type of surfactants have even an advantage over the currently used glucamides surfactants, since the glucamides surfactants will give N-glycosides after degradation of the amide bond, a product which is not easily biodegradable. Therefore, the new surfactants are much more mild and user friendly.

Accordingly, there is a need for such a composition of matter for surfactants, that can be used in detergents, pharmaceutical, medicinal, cosmetics and food industry, and a process to produce such compositions of matter in an efficient and high yield fashion.

SUMMARY OF THE INVENTION

The present invention provides for a novel composition of matter and a new method for the preparation of the novel composition of matter. The new structural type of nonionic surfactants having amide or ester bonds linking a hydrophilic component to a lipophilic or hydrophobic component are thought to be more mild and user friendly than the currently available surfactants. As important is the need for a convenient and feasible method to prepare such type of surfactants. The present surfactants are ideally suited for use in the food, pharmaceutical, medicinal and cosmetic fields.

The present invention provides a composition including a carbohydrate non-ionic, hydrophilic moiety and at least one non-ionic, hydrophobic hydrocarbon moieties.

The present invention provides a composition including a carbohydrate non-ionic, hydrophilic moiety and at least one non-ionic, hydrophobic hydrocarbon moieties having the general formula $$Z\text{-}(E\text{-}R)_n \quad (I)$$

where Z is a carbohydrate moiety including a hexose moiety, pentose moiety or mixture thereof, E is an amide linkage and/or an ester linkage and R are independently a hydrogen atom or a carbyl group having between about between 1 and 40 carbon atoms and the required hydrogen atoms to satisfy the valence and where one or more of the carbon atoms can be replaced by one or more hetero atoms selected from the group consisting of boron, nitrogen, oxygen, phosphorus, sulfur or mixture or combinations thereof and where one or more of the hydrogen atoms can be replaced by one or more single valence atoms selected from the group consisting of fluorine, chlorine, bromine, iodine or mixtures or combinations thereof.

The present invention provides a method including the step of contacting a nitrile compound of the general formula R—CN, where R is as described above and a carbohydrate non-ionic, hydrophilic moiety and at least one non-ionic, hydrophobic hydrocarbon moieties.

DETAILED DESCRIPTION OF THE INVENTION

The inventors have found a new class of non-ionic surfactants can be prepared in a simple one-pot reaction, where the surfactants are carbohydrate based.

Compositions

The invention encompasses a novel composition of matter consisting of carbohydrate-containing nonionic surfactants, including a variety of structural combinations between carbohydrate molecules and hydrocarbon groups, where the carbohydrate component is selected from the group consisting of any carbohydrate. Exemplary examples include, without limitation, glucose, galactose, mannose, and other hexoses or arabinose, ribose and other pentoses or their derivatives, including acyl, benzoyl protected esters or alkyl and acyl protected glycosides. The carbyl groups or hydrocarbon chains can contain from 1 to 40 carbon atoms. In other embodiments, the carbyl or hydrocarbon groups include from 2 to 24 carbon atoms. In other embodiments, the carbyl or hydrocarbon groups include from 4 to 16. In other embodiments, the carbyl or hydrocarbon groups include 6 to 14. In addition, the carbyl or hydrocarbon groups can be a either saturated or unsaturated, can be linear or branched, can include saturated or unsaturated ring, and/or can include aromatic ring as a part of their structures. Again, the groups include the required hydrogen atoms to satisfy the valence and where one or more of the carbon atoms can be replaced by one or more hetero atoms selected from the group consisting of boron, nitrogen, oxygen, phosphorus, sulfur or mixture or combinations thereof and where one or more of the hydrogen atoms can be replaced by one or more single valence atoms selected from the group consisting of fluorine, chlorine, bromine, iodine or mixtures or combinations thereof The linkage between the carbohydrate component and hydrophobic component, i.e., the hydrocarbon group, can be either an amide bond or ester bond.

For the new nonionic surfactants with only one hydrocarbon group as the hydrophobic component, the hydrophobic components can connect to the carbohydrate moiety at any of the hydroxyl groups within carbohydrate carbon backbone. In certain embodiments, the linkage occurs at position 1 or 6 in a hexose carbohydrate. In other embodiments, the linkage occurs at position 1 or 5 in a pentose carbohydrate. In yet other embodiments, the linkage occurs at position 1 of the carbohydrate molecule. The linkage between the carbohydrate and hydrophobic component can be an ester bond or an amide bond, preferentially an amide bond at position 1 or ester bond at any other hydroxyl group sites of the carbohydrates. Of course, the surfactant compositions of this invention can include one or a plurality of composition of formula (I).

However, for the new nonionic surfactants with more than one hydrocarbon chain as the hydrophobic component, the hydrocarbon group can link to carbohydrate via an amide bond or an ester bond. In certain embodiments, the hydrocarbon group are linked to the carbohydrate via an amide bond linkage at position 1 of carbohydrate and via ester linkages at any other position of carbohydrate.

Process

The novel process to produce the above described novel composition of matter is meant to be straightforward to those skilled in the art. The reaction can proceed in an inert reaction solvent or without any solvent at all. In this process, an acid is used as a promoter. The acid can be a Lewis acid. In certain embodiments, the acid is an ester of trifluoromethylsulfuric acid. In other embodiments, the acid is trimethylsilyl trifluoromethylsulfate (TMSOTf). The reaction can be performed in the presence or absence of a group IB metal salt. In certain embodiments to improve reaction yields, a group IB metal salt is present to maximize the function of acid. Exemplary examples of such group IB metal salts include, without limitation, copper salts, silver salts and/or gold salts. In certain embodiments, silver and/or gold salts are used. In other embodiments, a silver salt is used. The counter ion can have charge of −1 or −2. In certain embodiments, the charge is −1. Exemplary examples of such counter ions include, without limitaion, tetrafluoroborate, periodate, perchlorate, or mixtures or combinations thereof. In certain embodiments, the counter ion is perchlorate. The reaction can be carried out at a temperature range from about 40° C. to about 250° C. In certain embodiments, the temperature range is from about 0° C. to about 80° C. In certain embodiments, the temperature range is from 10° C. to 60° C. In certain embodiments, the temperature range is room temperature.

The starting material carbohydrate can be a native carbohydrate, for example any of monosaccharides such as hexoses (e.g., glucose, mannose, galactose, etc.) and pentoses (e.g., arabinose, ribose, etc.). On the other hand, the starting material carbohydrate can also be a protected carbohydrate, and the protecting groups on the carbohydrates can be an acyl group or an ether group.

In certain embodiments, the protecting group(s) is(are) an acyl group(s). In other embodiments, the protecting groups are acetyl groups ane/or benzoyl groups. In addition, the starting material carbohydrate can also be alkyl glycoside, either protected or unprotected where the protecting group can be acyl group and/or benzoyl group, and the alkyl group can be any of hydrocaryl group. In certain embodiments, the alkyl group is an alkyl group having between 1 and 3 carbon atoms and the required number of hydrogen atoms to complete the valency. In other embodiments, the alkyl group is ethyl or methyl. In yet other embodiments, the alkyl group is a methyl group.

When acyl protected carbohydrates are used in the described new reaction, only one hydrocarbon chain will be attached to the protected carbohydrate even when large excess amount of nitrites are used. However, when free carbohydrates (native state) are used, in the presence of excess amount of nitrites, one or two hydrocarbon chains may be attached to the carbohydrate component.

The starting material nitrites can be any compounds containing one or more than one nitrile or cyanide functional group. The nitrile functional group will react with the carbohydrate in the presence of an acid, preferentially in the presence of a group IB metal salt, to form either the amide bond or ester bond, most likely form the amide bond at position 1 of carbohydrate when the hydrocarbon chain connects with carbohydrate, or ester bond when hydrocarbon chain links to any other hydroxyl groups of carbohydrate. The rest of the nitrites' structure can be a long or short hydrocarbon group having between 1 and 40 carbon atoms. In certain embodiments, the hydrocarbon group includes from 1 to 24 carbon atoms. In certain embodiments, the hydrocarbon group includes from 4 to 16 carbon atoms. In certain embodiments, the hydrocarbon group includes from 5 to 13 carbon atoms. The group can be acyclic either linear or branched, cyclic either saturated, unsaturated or aromatic, mixed having cyclic and acyclic moieties. Of course, each surfactant can include a combination of these groups.

The process can also be carried out in any inert solvent. Exemplary examples of such solvents include, without limitation, hydrocarbon solvent, e.g., as pentane, hexane, cyclohexane, etc., chlorinated solvents, e.g., tetrachloromethane, chloroform, dichloromethane, 1,2-dichloroethane, etc. or mixture or combinations thereof. In certain embodiments, the solvent is a chlorinated solvent, if solvent is necessary. In other embodiments, the solvent is dichloromethane, if a solvent is used.

The amount of acid can be from a catalytic amount to more than two equivalents per mole of carbohydrate. In certain embodiments, the acid range is about half an equivalent (0.5) to 1.5 equivalents. The amount of group IB metal salt can be from catalytic amount to about 2 equivalents per mole of carbohydrate.

The process is carried out on an efficient mixing or agitating equipment, such as a high-speed stir or shaker, so that the solid carbohydrate can mix well with liquid nitrites if no solvent is added. If solvent is used, both carbohydrate and group IB salt are not soluble in the inert solvent, and the application of such efficient mixing equipment is more important.

The process can be generally represented with a reaction scheme below.

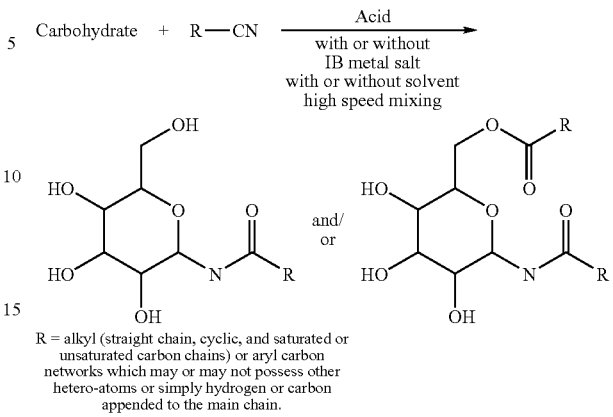

R = alkyl (straight chain, cyclic, and saturated or unsaturated carbon chains) or aryl carbon networks which may or may not possess other hetero-atoms or simply hydrogen or carbon appended to the main chain.

The carbohydrate component may exist as either a six-membered ring or a five-membered ring, i.e., the carbohydrate component may be in the form of either pyranoside or furanoside.

EXPERIMENTS OF THE INVENTION

The structures of nonionic surfactants are evidenced by the high field NMR (600 MHz, Brucker) spectra of derivatives obtained from the acetylation of the prepared novel surfactant molecules.

Example 1

The acetylated derivative (1-deoxy-1-acetyamido-2,3,4,6-tetraacetyl-β-D-glucopyranose) from the reaction between glucose and acetonitrile:

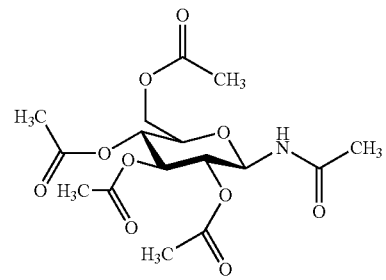

To a 20 mL of glass vial, was added 0.225 g of glucose, 4.0 mg of $AgClO_4$, 10 mL of $CH_3CN$ and 0.3 mL of TMSOTf, the color turned to yellow. The vial was sealed and bound to a high-speed shaker and shaken at temperature between 0 to 60° C. Within 7 hrs, all solid disappeared, and the solution turned to rose or red purple. The reaction was monitored by TLC and only a major product was detected by TLC. After 24 hrs, the solution was simply loaded to a 10 cm silica gel, and eluted using EtOAc:MeOH (3:1) to obtain a oily residue. To this reside was added 2 mL of pyridine and 2 mL of acetic anhydride, and the mixture was stirred for overnight. Then the mixture was mixed with 100 mL of EtOAc, washed with 1N HCl, saturated $NaHCO_3$ and brine, dried over $CaCl_2$. After removal of solvent, the residue was loaded on a silica gel and eluted with hexane:EtOAc (5:1 to 3:2) to obtain 0.113 g of final product, i.e., 1-deoxy-1-β-acetyamido-2,3,4,6-tetraacetyl-D-glucopyranose with overall yield of 23.2% for two reaction steps and two purification processes: $^1$H NMR ($CDCl_3$, 600 MHz) δ (ppm) 6.72 (d, J=9.3 Hz, 1H, NH), 5.31

(d-d, $J_1=J_2=9.48$ Hz, 1H, H-3), 5.29 (d-d, $J_1=9.43$ Hz, $J_2=9.25$ Hz, 1H, H-1), 5.06 (d-d, $J_1=J_2=9.75$ Hz, 1H, H-4), 4.93 (d-d, $J_1=J_2=9.55$ Hz, 1H, H-2), 4.31 (d-d, $J_1=12.47$ Hz, $J_2=4.44$ Hz, 1H, H-6), 4.09 (d, J=12.47 Hz, 1H, H-6), 3.86 (d-d-d, $J_1=10.02$ Hz, $J_2=2.22$ Hz, $J_3=1.82$ Hz, 1H, H-5), 2.08 (s, 3H, Ac), 2.06 (s, 3H, Ac), 2.04 (s, 3H, Ac), 2.02 (s, 3H, Ac), 2.00 (s, 3H, Ac). $^{13}$C NMR (CDCl$_3$, 125 MHz) δ (ppm): 170.60 (CO), 170.43 (2 CO), 169.66 (CO), 169.40 (CO), 77.88 (C-1), 73.30 (C-5), 72.67 (C-3), 70.42 (C-2), 67.99 (C-4), 61.56 (C-6), 23.06 (CH$_3$), 20.50 (CH$_3$), 20.43 (CH$_3$), 20.36 (CH$_3$), 20.34 (CH$_3$).

Example 2

The acetylated derivative from the reaction between glucose and cyclopropyl nitrile: The reaction was set up similar to the example 1. To a 20 mL vial, was added 0.225 g of glucose, 1.5 mL of cyclopropyl cyanide, 0.135 g of AgClO$_4$, and 0.5 mL of TMSOTF. After shaking for 3 hrs, all glucose solid disappeared. After 24 hrs, 0.5 mL of Et$_3$N was added, and a clear green solution was obtained. The mixture was loaded to silica gel column directly, and purified using hexane:EtOAc (2:1 to 1:1) to remove excess cyclopropyl cyanide first, then followed by EtOAc:MeOH (5:1) to obtain two fractions: fraction 1: $R_f$=0.81 (EtOAc:MeOH=3:1), 0.219 g after dried under vacuum for 2 days; fraction 2: $R_f$=0.41 (EtOAc:MeOH=3:1), 0.223 g after dried under vacuum for 2 days. The calculated yield based on the fractions weight was more than 100%, probably the solvent was not completely removed; however, the yield should be above 85% according to TLC. Fraction 1 was characterized to carry two hydrocarbon chains with one chain at position 1 and the second at any other hydroxyl groups. Although it is difficult to judge the exact location of second hydrocarbon chain on the ring, it is likely that the second chain is on position 6 because primary OH is more reactive than secondary OH in carbohyhdrate. On the basis of coupling constants between the protons on carbohydrate ring, it is believed that furanosidic ring is more likely to exist in fraction 1 rather than the pyranosidic ring. The fraction 2 was acetylated and purified using similar procedure as in example 1, and was characterized to hold only one hydrocarbon chain at position 1 in a pyranosidic ring. The structures of two derivatives are characterized by NMR spectra as below:

Fraction 1: 1-deoxy-1-cyclopropylformamido-6-cyclopropylformyl-β-D-glucofuranoside

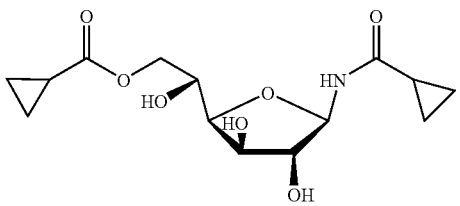

$^1$H NMR (CDCl$_3$, 600 MHz), δ (ppm): 6.14 (d, J=9.96 Hz, 1H, NH), 6.00 (d-d, $J_1$=10.16 Hz, $J_2$=3.32 Hz, 1H, H-1), 5.05-5.07 (multi, 2H, H-2, H-5), 4.78 (d-d, $J_1$=$J_2$=5.27 Hz, 1H, H-3), 4.31 (d, J=5.02 Hz, 1H, H-4), 3.86 (d-d, $J_1$=10.09 Hz, $J_2$=4.5 Hz, 1H, H-6), 3.82 (d-d, $J_1$=10.09 Hz, $J_2$=5.51 Hz, 1H, H-6), 1.68-1.70 (multi, 1H, CH), 1.57-1.60 (br, 3H, OH), 1.29-1.31 (multi, 1H, CH), 0.95-0.97 (multi, 4H), 0.83-0.86 (multi, 2H), 0.74-0.75 (multi, 2H). $^{13}$C NMR (CDCl$_3$, 125 MHz).

Acetylated derivative from fraction 2: 1-deoxy-1-α-cyclopropylformamido-2,3,4,6-tetraacetyl-D-gluco-furanoside:

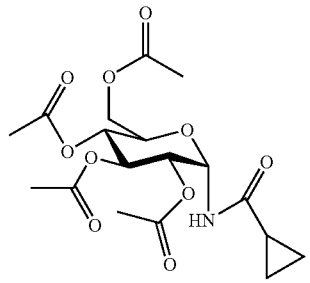

$^1$H NMR (CDCl$_3$, 600 MHz), δ (ppm): 6.99 (d, J=6.19 Hz, 1H, NH), 5.82 (s, 1H, H-1), 5.35 (d-d, $J_1$=9.64 Hz, $J_2$=8.79 Hz, 1H, H-3), 5.11 (d-d, $J_1$=9.19 Hz, $J_2$=5.00 Hz, 1H, H-2), 5.01 (d-d, $J_1$=$J_2$=9.70 Hz, 1H, H-4), 4.25 (d-d, $J_1$=12.34 Hz, $J_2$=4.15 Hz, 1H, H-6), 4.00 (d, J=12.49 Hz, 1H, H-6), 3.91 (d, J=7.16 Hz, 1H, H-5), 2.01 (s, 3H, Ac), 1.98 (s, 3H, Ac), 1.97 (s, 6H, 2Ac), 1.47 (br, 1H, CH), 0.96-1.02 (br, 2H), 0.73-0.79 (multi, 2H).

Example 3

The product of reaction between 1,2,3,4,6-pentaacetyl glucose and undecyl nitrile To a 20 mL of vial, was added 0.2169 g of 1,2,3,4,6-pentaacetyl β-D-glucose and 1.0 mL of undecyl cyanide, 0.1048 g of AgClO$_4$, and 0.5 mL of TMSOTf. The vial was sealed and shaken for 24 hrs. The mixture was monitored by TLC and only one major product was identified on TLC. The mixtures was directly loaded to silica gel to separate 1-deoxy-1-β-lauroamido-2,3,4,6-tetraacetyl-glucopyranoside:

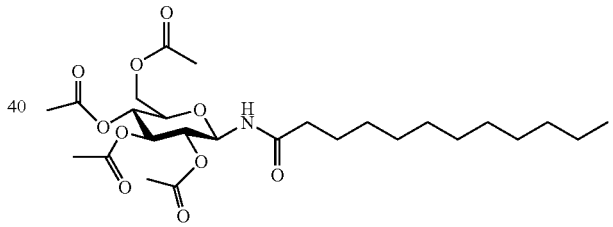

$^1$H NMR (CDCl$_3$, 600 MHz), δ (ppm): 6.20 (d, J=9.32 Hz, 1H, NH), 5.30 (d-d, $J_1$=J2=9.46 Hz, 1H, H-3), 5.25 (d-d, $J_1$=$J_2$=9.40 Hz, 1H, H-1), 5.05 (d-d, $J_1$=$J_2$=9.70 Hz, 1H, H-4), 4.91 (d-d, $J_1$=$J_2$=9.54 Hz, 1H, H-2), 4.31 (d-d, $J_1$=12.50 Hz, $J_2$=4.15 Hz, 1H, H-6), 4.06 (d, J=12.28 Hz, 1H, H-6), 3.81 (d-d-d, $J_1$=9.97 Hz, $J_2$=0.97 Hz, $J_3$=0.85 Hz, 1H, H-5), 2.10-2.20 (multi, 2H), 2.07 (s, 3H, Ac), 2.03 (s, 3H, Ac), 2.02 (s, 3H, Ac), 2.01 (s, 3H, Ac), 1.56-1.59 (multi, 2H), 1.24-1.29 (mutli, 16 H), 0.87 (t, J=6.52 Hz, 3H, CH$_3$). $^{13}$C NMR (CDCl$_3$, 125 MHz), δ (ppm): 173.39 (CO), 171.01 (CO), 170.59 (CO), 169.83 (CO), 169.55 (CO), 78.11 (C-1), 73.51 (C-5), 72.64 (C-3), 70.57 (C-2), 68.13 (C-4), 61.61 (C-1), 36.65 (CH$_2$), 29.55 (Ac), 29.41 (Ac), 29.26 (Ac), 29.07 (Ac), 25.12, 22.64, 20.70, 20.61, 20.55, 14.07 (CH$_3$).

Example 4

The acetylated derivative from the reaction between glucose and 4-methyl benzyl cyanide To a 20 mL of vial, was added 0.2418 g of glucose, 0.1244 g of AgClO$_4$, 1.5 mL of 4-methyl-benzyl cyanide, and 0.5 mL of TMSOTf. The mixture was shaken for 24 hrs. and monitored by TLC, and only one major product was identified. After purified from silica gel column (hexane:EtOAc=2:1 to 1:1, then EtOAc:MeOH=5:1), one major fraction was obtained ($R_f$=0.80, EtOAc:MeOH=3:1) that was acetylated with pyridine and acetic anhydride, and give 1-deoxy-1-(α-tolyl)-acetoamido-2,3,4-triacetyl-6-(α-tolyl)-acetyl-β-D-glucopyranoside after column purification (hexane:EtOAc=3:1):

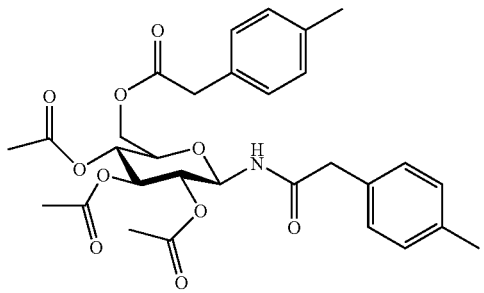

$^1$H NMR (CDCl$_3$, 600 MHz), δ (ppm): 7.01-7.14 (multi, 8H, Ph), 6.45 (d, J=7.25 Hz, 1H, NH), 5.75 (d-d, $J_1$=$J_2$=6.55 Hz, 1H, H-1), 5.23 (d-d, $J_1$=$J_2$=9.65 Hz, 1H, H-3), 5.01 (d-d, $J_1$=10.08 Hz, $J_2$=5.26 Hz, 1H, H-2), 4.90 (d-d, $J_1$=9.81 Hz, $J_2$=9.49 Hz, 1H, H-4), 4.18 (d-d, $J_1$=12.41 Hz, $J_2$=4.18 Hz, 1H, H-6), 4.02 (d, J=11.18 Hz, 1H, H-6), 3.79 (d, J=8.72 Hz, 1H, H-5), 3.52 (s, 2H, CH$_2$), 3.46 (s, 2H, CH$_2$), 2.24 (s, 6 H, 2 CH$_3$), 1.91 (s, 3H, CH$_3$), 1.84 (s, 3H, CH$_3$), 1.79 (s, 3H, CH$_3$). $^{13}$C NMR (CDCl$_3$, 125 MHz), δ (ppm): 171.53 (CO), 170.71 (CO), 170.43 (CO), 169.65 (CO), 169.30 (CO), 137.05 (Ph), 130.03 (Ph), 129.66 (Ph), 129.42 (Ph), 129.20 (Ph), 128.86 (Ph), 127.78 (Ph), 74.07 (C-1), 69.95 (C-3), 68.50 (C-2), 68.27 (C-4), 68.00 (C-5), 61.99 (C-6), 40.72 (CH$_2$), 40.38 (CH$_2$), 22.99 (CH$_3$), 20.96 (2CH$_3$), 20.49 (2CH$_3$). The slightly small coupling constant between H-1 and H-2 is probably because of a large group at position 1.

Example 5

The acetylated derivative from the reaction between galactose and 4-methyl benzyl cyanide To a 20 mL of vial, was added 0.2616 g of D-galactose, 1.6 mL of 4-methy benzyl cyanide, 0.1605 g of AgClO$_4$ and 0.7 mL of TMSOTf. The mixture was shaken for 2 days, and only a little amount of precipitate present (might be AgClO$_4$). Two major products were identified by TLC which are not separated by column but subjected to the acetylation to prepare the derivatives, though the yield of this step is more than 85%. After acetylation with pyridine and acetic anhydride, the mixture was mixed with EtOAc, and washed with HCl, saturated NaHCO$_3$ and brine, dried and evaporated to give viscous residue, that was further purified by column chromatography, using hexane:EtOAc (3:2) as eluent to give the product with two hydrocarbon chain: 1-deoxy-(α-tolyl)acetoamido-2,3,5-triacetyl-6-(α-tolyl)acetyl-β-glactofuranoside:

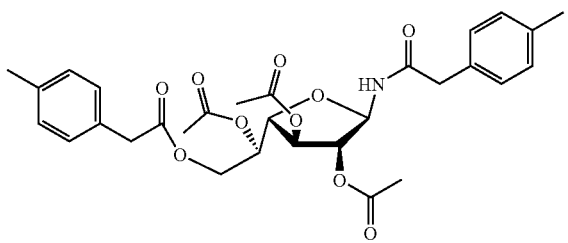

$^1$H NMR (CDCl$_3$, 600 MHz), δ (ppm): 7.15 (d, J=8.99 Hz, 1H, 2H, Ph), 7.04-7.11 (multi, 3H, Ph), 6.97-7.03 (multi, 2H, Ph), 6.95 (d, J=8.02 Hz, 1H, Ph), 5.84 (d-d, $J_1$=9.94 Hz, $J_2$=4.35 Hz, 1H, H-1), 5.65 (d, J=9.92 Hz, 1H, NH), 5.20 (d-d-d, $J_1$=9.80 Hz, $J_2$=3.82 Hz, $J_3$=3.01 Hz, 1H, H-5), 5.08 (d, J=3.80 Hz, 1H, H-2), 4.94 (d-d, $J_1$=1.40 Hz, $J_2$=1.27 Hz, 1H, H-3), 4.24 (d-d, $J_1$=12.16 Hz, $J_2$=3.72 Hz, 1H, H-6), 3.95 (d-d, $J_1$=12.17 Hz, $J_2$=6.78 Hz, 1H, H-6), 3.81 (d-d, $J_1$=7.02 Hz, $J_2$=3.02 Hz, 1H, H-4), 3.62 (d, J=14.44 Hz, 1H), 3.56 (d, J=14.41 Hz, 1H), 2.25 (d, J=3.26 Hz, 1H), 2.22 (s, 3H, CH$_3$), 2.20 (d, J=3.61 Hz, 1H), 2.01 (s, 3H, CH$_3$), 1.98 (s, 3H, CH$_3$), 1.95 (s, 3H, CH$_3$), 1.57 (s, 3H, CH3). $^{13}$C NMR (CDCl$_3$, 125 MHz), δ (ppm): 170.55 (CO), 170.28 (CO), 169.85 (CO), 169.47 (CO), 169.31 (CO), 137.33 (Ph), 130.32 (Ph), 129.68 (Ph), 129.34 (Ph), 129.08 (Ph), 128.83 (Ph), 127.73 (Ph), 79.73 (C-1), 79.44 (C-4), 76.26 (C-3), 74.60 (C-2), 69.86 (C-5), 62.61 (C-6), 40.98 (CH$_2$), 22.82 (CH$_3$), 20.93 (CH$_3$), 20.87 (CH$_3$), 20.56 (CH$_3$).

Example 6

The acetylated derivative from the reaction between galactose and cyclopropyl cyanide To a 20 mL of vial, was added 0.3148 g of D-galactose, 1.6 mL of cyclopropyl cyanide, 0.1062 g of AgClO$_4$ and 0.7 mL of TMSOTf. The mixture was shaken for 2 days and monitored by TLC. Two major products were detected on TLC and they are separated on silica gel column using hexane:EtOAc=2:1 to 1:1 then EtOAc:MeOH (5:1) to obtain two fractions: fraction 1 ($R_f$=0.73 (EtOAc:MeOH=3:1), and fraction 2 ($R_f$=0.54 (EtOAc:MeOH=3:1)), where fraction 1 was more than 60% of total weight. Both fractions were acetylated using pyridine and acetic anhydride, after extraction with EtOAc and washed with HCl, NaHCO$_3$ and brine, the residues upon removal of solvent were chromatogrphed on silica gel using hexane:EtOAc (5:1 to 1:2). The residue of fraction 1 give one major produt with $R_f$=0.26 (hexane:EtOAc=1:2) as 1-deoxy-1-cyclopropylformamido-2,3,4-triacetyl-6-cyclopropylformyl-β-galactopyranoside.

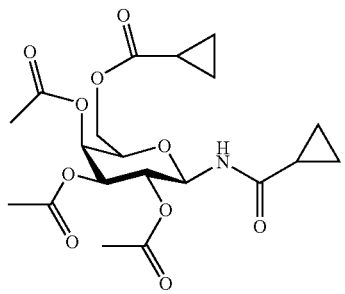

$^1$H NMR (CDCl$_3$, 600 MHz), δ (ppm): 6.53 (d, J=9.67 Hz, 1H, NH), 5.92 (d-d, $J_1$=9.73 Hz, $J_2$=4.84 Hz, 1H, H-1), 5.23 (d-d, $J_1$=4.34 Hz, $J_2$=3.35 Hz, 1H, H-3), 5.17 (d-d, $J_1$=4.80 Hz, $J_2$=3.34 Hz, 1H, H-2), 4.17 (d-d, $J_1$=11.60 Hz, $J_2$=7.46 Hz, 1H, H-6), 4.08 (d-d, $J_1$=11.60 Hz, $J_2$=4.25 Hz, 1H, H-6), 4.02-4.04 (multi, 1H, H-5), 3.80 (d-d, $J_1$=4.37 Hz, $J_2$=2.49 Hz, 1H, H-4), 2.04 (s, 6H), 1.98 (s, 6H), 1.51-1.60 (multi, 2H, 2 CH), 0.98-1.00 (multi, 2H), 0.93-0.95 (multi, 2H), 0.87-0.89 (multi, 2H), 0.81-0.84 (multi, 2H). $^{13}$C NMR (CDCl$_3$, 125 MHz) δ (ppm): 175.15 (CO), 173.40 (CO), 170.26 (CO), 169.92 (CO), 81.13 (C-4), 78.95 (C-1), 76.54 (C-3), 75.40 (C-2), 68.98 (C-5), 65.82 (C-6), 23.41 (CH$_3$), 20.72 (CH$_3$), 12.74 (CH), 12.59 (CH), 9.22 (CH$_2$), 8.76 (CH$_2$). However, in fraction 2 after acetylation and similar purification process, three products were identified from TLC, and after column chromatography, the major product with $R_f$=0.24 (hexane:EtOAc=1:2) was characterized as 1-deoxy-1-cyclopropylformamido-2,3,5,6-tetraacetyl-β-D-galactofuranoside:

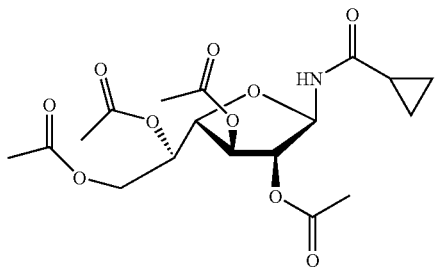

¹H NMR (CDCl₃, 600 MHz), δ (ppm): 6.33 (d, J=9.70 Hz, 1H, NH), 5.99 (d-d, J₁=9.83 Hz, J₂=4.40 Hz, 1H, H-1), 5.29 (d-d, J₁=9.37 Hz, J₂=6.55 Hz, 1H, H-5), 5.13 (d, J=4.28 Hz, 1H, H-2), 5.01 (s, 1H), 4.33 (d-d, J₁=12.07 Hz, J₂=3.57 Hz, 1H), 4.05 (d-d, J₁=11.98 Hz, J₂=6.90 Hz, 1H, H-6), 3.86 (d-d, J₁=6.38 Hz, J2=3.14 Hz, 1H, H-4), 2.14 (s, 3H, CH₃), 2.06 (s, 3H, CH₃), 2.04 (s, 3H, CH₃), 1.99 (s, 3H, CH₃), 1.31-1.35 (multi, 1H), 0.75-0.98 (multi, 4H). ¹³C NMR (CDCl₃, 125 MHz), δ (ppm): 173.61 (CO), 170.58 (CO), 170.48 (CO), 169.62 (CO), 168.98 (CO), 79.63 (C-1), 79.37 (C-4), 76.44 (C-3), 74.97 (C-2), 70.03 (C-5), 62.70 (C-6). 20.96 (CH₃), 20.72 (CH₃), 20.66 (CH₃), 14.93 (CH), 8.14 (CH₂), 8.05 (CH₂).

Other two products were identified to not carrying amide functional groups and are not included here.

Example 7

The acetylated derivative from the reaction between galactose and n-heptyl cyanide To a 20 mL of vial, was added 0.2559 g of D-galactose, 1.6 mL of n-heptyl cyanide, 0.1711 g of AgClO₄ and 0.7 mL of TMSOTf, the mixture was shaken for 2 days. The reaction mixture was identified to carried two major spots on TLC with R$_f$=0.90 and 0.76 respectively (EtOAc:MeOH=10:1). Another minor spot with R$_f$=0.55 (EtOAc:MeOH) was characterized to not carry amide bond after derivatization and purification. The two major products were roughly purified from the minor spot on TLC and acetylated using pyridine and acetic anhydride at −78° C., after regular workup procedure similar to above, the residue was separated by column chromatography, and two major fractions were collected with R$_f$=0.66 (hexane:EtOAc=1:2) and 0.26 (hexane:EtOAc=1:2) respectively, the former one was identified as the molecule with two hydrocarbon chain and the latter carrying only one hydrocarbon chain. According to the NMR spectra, they are assigned as furanosides rather than pyranosides as characterized below, 1-deoxy-1-octoylamido-2,3,5-triacetyl-6-octoyl-b-D-galactofuranoside:

¹H NMR (CDCl₃, 600 MHz), δ (ppm): 6.17 (d, J=9.75 Hz, 1H, NH), 5.99 (d-d, J₁=9.80 Hz, J₂=4.19 Hz, 1H, H-1), 5.27 (d-d-d, J₁=9.79 Hz, J₂=3.69 Hz, J3=3.41 Hz, 1H, H-5), 5.15 (d-d, J₁=6.35 Hz, J₂=4.31 Hz, 1H, H-2), 5.00 (d, J=7.56 Hz, 1H, H-3), 4.34 (d-d, J₁=12.05 Hz, J₂=3.46 Hz, 1H, H-6), 4.03 (d-d, J₁=12.09 Hz, J₂=6.58 Hz, 1H, H-6), 3.85 (d-d, J₁=7.05 Hz, J₂=2.54 Hz, 1H, H-4), 2.37 (t, J=7.64 Hz, 2H, CH₂), 2.22 (t, J=7.54 Hz, 2H, CH₂), 2.05 (s, 3H, Ac), 3.04 (s, 3H, Ac), 1.96 (s, 3H, Ac), 1.51-1.62 (multi, 4H), 1.22 (br, 16 H), 0.81 (t, J=6.14 Hz, 6H, 2CH₃). ¹³C NMR (CDCl₃, 125 MHz), δ (ppm): 173.33 (CO), 171.75 (CO), 170.55 (CO), 169.89 (CO), 169.60 (CO), 79.73 (C-1), 79.48 (C-4), 76.56 (C-3), 74.47 (C-2), 70.07 (C-5), 62.44 (C-6), 33.94 (CH₂), 31.59 (CH₂), 28.99, 28.89, 24.72, 24.69, 23.42, 22.56, 20.98, 20.67, 14.04 (CH₃).

1-deoxy-1-octoylamido-2,3,6-triacetyl-β-D-galactopyranoside (possibly 4-OH on carbohydrate not protected by acetyl group because of low reaction temperature)

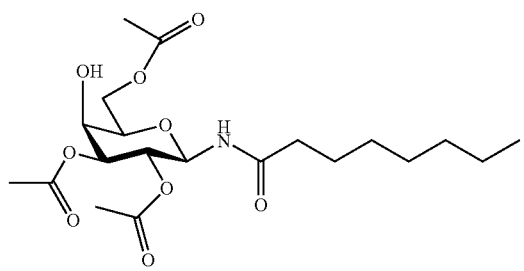

¹H NMR (CDCl₃, 600 MHz), δ (ppm): 6.51 (d, J=9.70 Hz, 1H, NH), 5.92 (d-d, J₁=9.73 Hz, J₂=4.72 Hz, 1H), 5.18 (d-d, J₁=4.06 Hz, J₂=3.54 Hz, 1H, H-3), 5.15 (d-d, J₁=4.07 Hz, J₂=3.89 Hz, 1H, H-2), 4.16 (d-d, J₁=11.37 Hz, J₂=7.45 Hz, 1H, H-6), 4.05 (d-d, J₁=11.43 Hz, J₂=4.34 Hz, 1H, H-6), 4.02 (d, J=4.82 Hz, 1H, H-5), 3.78 (d-d, J₁=4.27 Hz, J₂=2.39 Hz, 1H, H-4). 2.30 (t, J=7.60 Hz, 2H, CH₂), 2.05 (s, 3H), 2.02 (s, 3H), 1.97 (s, 3H), 1.56 (quint, 2H), 1.20-12.3 (multi, 8H), 0.81 (t, J=6.52 Hz, 3H, CH3). ¹³C NMR (CDCl₃, 125 MHz), δ (ppm): 172.22 (CO), 171.20 (CO), 170.30 (CO), 170.00 (CO), 81.04 (C-4), 78.82 (C-1), 76.45 (C-3), 75.07 (C-2), 68.78 (C-5), 65.63.(C-6), 33.85 (CH₂), 31.57 (Ac), 28.96 (Ac), 28.86 (Ac), 24.64 (CH₂), 23.42 (CH₂), 22.54 (CH₂), 20.84 (CH₂), 20.74 (CH₂), 14.03 (CH₃). (The small coupling constants between H-2 and H-3 and H-1 and H-2 are probably because of the long chain on position 1).

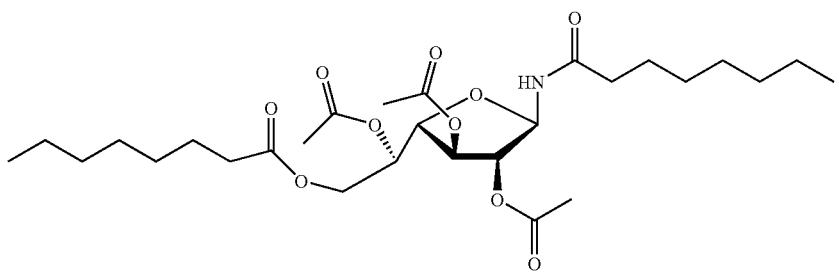

REFERENCE

The following references are cited in this application:
1. Tsujii, K. *Surface Activity, Principles, Phenomena, and Applications,* Academic Press, San Diego, 1998. p 15.
2. ibid, p 42.
3. ibid, pp 44-81.
4. ibid, pp 83-129.
5. Nelson, D. L. and Cox, M. M., *Lehninger's Principles of Biochemistry,* 4$^{th}$ edition, W. H. Freeman and Company, New York, 2005, p 372.
6. Schramm, L. L.; Stasiuk, E. N. and Marangoni, D. G., *Annu. Rep. Prog. Chem., Sect. C,* 2003, 99, 3-48.
7. www.kcpc.usyd.edu.au/discovery/9.5.5/9.5.5_emulsions2.html
8. a) Rosen, M. J.; Friedman, D. and Gross, M., *J. Phys. Chem.,* 1964, 68, 3219. b) Kolp, D. G.; Laughlin, R. G.; Krause, F. P. and Zimmerer, R. E., *J. Phys. Chem.,* 1963, 67, 51.
9. Ref 1, p 178.
10. Ref 1, p24.
11. Ref 1, pp 165-166.
12. Bevinakatti, H. S. and Mishra, B. K., "*Sugar Derived Surfactants*" in *Design and Selection of Performance Surfactants,* Edited by Karsa, D. R., Sheffield Academic Press, 1999, pp 1-50.
13. a) Scheibel, J. J.; Connor, D. S.; Shumate, R. E.; St. Laurent, J. and Theophile, R. B., *Process for preparing N-alkyl polyhydroxy amines and fatty acid amides therefrom in hydroxy solvents.* 1992, PCT Int. Appl. WO 92 06984, assigned to Procter & Gamble. b) Kao, J. N.; Scheibel, J. J.; Shumate, R. E.; Stark, C. M.; Severson, R. G.; Garber, K. L. and Vandiest, S. A., *Preparation of N-alkylpolyhydroxyalkaneamines, especially N-methylglucamine, in water and/or hydroxy containing solvent.* 1993, PCT Int. Appl. WO 93 03, 004, Procter & Gamble. c) Beck, R. H.; Kalff, N. J. and Roeper, H. W., *Process for the production of aminopolyols.* 1993, Eur. Pat. Appl. EP 536,939, Cerestar Holding.
14. Mehltretter, C. L.; Mellies, R. L. and Rankin, J. C., *Substituted gluconamides,* 1954, US Patent, U.S. Pat. No. 2,670,345, assigned to US Dept. of Agriculture.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

I claim:

1. A composition comprising at least one carbohydrate-containing nonionic surfactant compound of the general formula:

$$Z\text{-}(E\text{-}R)_n \quad (I)$$

where:
Z is a carbohydrate moiety including a five membered ring or six membered ring, at least one E group is an amide linkage attached to the 1 position of the Z group formed between the nitrogen atom of the amide linkage and the carbon atom located at a position 1 of the carbohydrate moiety when numbering the carbohydrate moiety clockwise from the ring oxygen atom, while the other E groups are ester linkages with the oxygen atom of the carbohydrate group bonded to the carbonyl group of the ester linkage;

R are independently a hydrogen atom or a carbyl group having between about 1 and 40 carbon atoms and the required hydrogen atoms to satisfy the valence and where one or more of the carbon atoms can be replaced by one or more hetero atoms selected from the group consisting of boron, nitrogen, oxygen, phosphorus, sulfur or mixture or combinations thereof and where one or more of the hydrogen atoms can be replaced by one or more single valence atoms selected from the group consisting of fluorine, chlorine, bromine, iodine or mixtures or combinations thereof; and n is an integer having a value from 1 to a number of hydroxy groups of the carbohydrate moiety prior to modification.

2. The composition of claim 1, wherein n has a value of at least two and the other non-polar hydrocarbon groups are attached to the hydroxy groups of carbohydrate moiety through an ester linkage.

3. The composition of claim 1, wherein the carbohydrate moiety includes a sugar residue selected from the group consisting of a hexose moiety, a pentose moiety and mixtures thereof.

4. The composition of claim 1, wherein the R groups independently are an acyclic, cyclic or mixed group having cyclic and acyclic moieties.

5. The composition of claim 1, wherein the R groups include a cyclic ring as a part of their structure.

6. The composition of claim 1, wherein the R groups include an aromatic ring as a part of their structure.

7. A process to prepare or produce non-ionic carbohydrate surfactants including the step of contacting a carbohydrate molecule including at least one cyclic sugar residue with a nitrile compound of the general formula R—CN to form a carbohydrate-containing nonionic surfactant comprising a compound of the general formula:

$$Z\text{-}(E\text{-}R)_n \quad (I)$$

where:
Z is a carbohydrate moiety including a five membered ring or six membered ring, at least one E group is an amide linkage attached to the 1 position of the Z group formed between the nitrogen atom of the amide linkage and the carbon atom located at a position 1 of the carbohydrate moiety when numbering the carbohydrate moiety clockwise from the ring oxygen atom, while the other E groups are ester linkages with the oxygen atom of the carbohydrate group bonded to the carbonyl group of the ester linkage, R groups are independently a carbyl group having between about 1 and 40 carbon atoms and the required hydrogen atoms to satisfy the valence and where one or more of the carbon atoms can be replaced by one or more hetero atoms selected from the group consisting of boron, nitrogen, oxygen, phosphorus, sulfur or mixture or combinations thereof and where one or more of the hydrogen atoms can be replaced by one or more single valence atoms selected from the group consisting of fluorine, chlorine, bromine, iodine or mixtures or combinations thereof, and n is an integer having a value from 1 to a number of hydroxy groups of the carbohydrate moiety prior to modification.

8. The process of claim 7, wherein the carbohydrate is acyl group protected or acyl group unprotected, where the acyl group is any fatty acid or benzoic acid.

9. The process of claim 7, wherein the carbohydrate is protected with ether bonds or is an protected or unprotected alkyl or aryl glycosides.

10. The process of claim 7, wherein the contacting is in the present of an acid, where the acid is a Lewis acid, perchloric acid or trimethylsilyl trifluoromethylsulfonate.

11. The process of claim 7, wherein the contacting is in the presence of a group IB metal salt.

12. The process of claim 7, wherein the contacting is in the presence of an inert solvent.

13. The process of claim 12, wherein the inert solvent is a hydrocarbon or chlorinated solvent.

14. The process of claim 7, wherein the contacting is performed using an efficient mixing system.

15. The process of claim 7, wherein the contacting is performed using an efficient mixing system.

16. The process of claim 1, wherein the composition is a non-ionic surfactant.

17. The process of claim 1, wherein the composition is a detergent.

18. The process of claim 1, wherein the composition is an emusilfier component.

19. The process of claim 1, wherein the composition is used for the construction of membranes or films.

20. The composition of claim 1, further comprising a plurality of protecting group attached to unreacted hydroxyl group of the carbohydrate moiety through ester linkages.

21. The composition of claim 20, wherein the protecting group are acyl or benzoyl groups.

22. The composition of claim 1, wherein the compounds of formula (I) are selected from the group consisting of 1-deoxy-1-acetyamido-2,3,4,6-tetra acetyl-β-D-glucopyranose, 1-deoxy-1-cyclopropylformamido-6-cyclopropylformyl-β-D-glucofuranoside, 1-deoxy-1-α-cyclopropylformamido-2,3,4,6-tetraacetyl-D-gluco-furanoside, 1-deoxy-1-β-lauroamido-2,3,4,6-tetra acetyl-glucopyranoside, 1-deoxy-1-(α-tolyl)-acetoamido-2,3,4-triacetyl-6-(α-tolyl)-acetyl-β-D-glucopyranoside, 1-deoxy-(α-tolyl)acetoamido-2,3,5-triacetyl-6-(α-tolyl)acetyl-β-glactofuranoside, 1-deoxy-1-cyclopropylformamido-2,3,4-triacetyl-6-cyclopropylformyl-β-galactopyranoside, 1-deoxy-1-cyclopropylformamido-2,3,5,6-tetraacetyl-β-D-galactofuranoside, 1-deoxy-1-octoylamido-2,3,5-triacetyl-6-octoyl-b-D-galactofuranoside, and 1-deoxy-1-octoylamido-2,3,6-triacetyl-β-D-galactopyranoside.

23. The process of claim 7, wherein the compounds of formula (I) are selected from the group consisting of 1-deoxy-1-acetyamido-2,3,4,6-tetra acetyl-β-D-glucopyranose, 1-deoxy-1-cyclopropylformamido-6-cyclopropylformyl-βD-D-glucofuranoside, 1-deoxy-1-α-cyclopropylformamido-2,3,4,6-tetraacetyl-D-gluco-furanoside, 1-deoxy-1-β-lauroamido-2,3,4,6-tetra acetyl-glucopyranoside, 1-deoxy-1-(α-tolyl)-acetoamido-2,3,4-triacetyl-6-(α-tolyl)-acetyl-β-D-glucopyranoside, 1-deoxy-(α-tolyl)acetoamido-2,3,5-triacetyl-6-(α-tolyl)acetyl-β-glactofuranoside, 1-deoxy-1-cyclopropylformamido-2,3,4-triacetyl-6-cyclopropylformyl-β-galactopyranoside, 1-deoxy-1-cyclopropylformamido-2,3,5,6-tetraacetyl-β-D-galactofuranoside, 1-deoxy-1-octoylamido-2,3,5-triacetyl-6-octoyl-b-D-galactofuranoside,and 1-deoxy-1-octoylamido-2,3,6-triacetyl-β-D-galactopyranoside.

* * * * *